United States Patent [19]

Lyons

[11] Patent Number: 4,617,287
[45] Date of Patent: Oct. 14, 1986

[54] RUTHENIUM-COBALT CARBONYL CATALYSTS FOR THE DEALKOXYHYDROXYMETHYLATION OF ALDEHYDE ACETALS TO FORM GLYCOL ETHERS

[75] Inventor: James E. Lyons, Wallingford, Pa.

[73] Assignee: Sun Refining and Marketing Company, Philadelphia, Pa.

[21] Appl. No.: 782,806

[22] Filed: Oct. 2, 1985

Related U.S. Application Data

[63] Continuation-in-part of Ser. No. 622,815, Jun. 21, 1984, abandoned.

[51] Int. Cl.$^4$ .......... B01J 27/20; B01J 31/20; C07C 41/01
[52] U.S. Cl. .................. 502/174; 502/161; 568/648; 568/670; 568/671; 568/675; 568/678
[58] Field of Search ............ 502/174, 161; 423/417, 423/418

[56] References Cited

U.S. PATENT DOCUMENTS 2,525,793 10/1950 Gresham et al. .............. 260/615
4,062,898 12/1977 Dubeck et al. ................ 260/632
4,226,845 10/1980 Laine ............................ 502/174
4,308,403 12/1981 Knifton ......................... 568/678
4,317,943 3/1982 Knifton ......................... 568/678
4,356,327 10/1982 Knifton ......................... 568/387
4,357,477 11/1982 Knifton ......................... 568/678
4,390,734 6/1983 Knifton ......................... 568/678
4,484,002 11/1984 Lin .............................. 502/161

Primary Examiner—P. E. Konopka
Attorney, Agent, or Firm—J. Edward Hess; Donald R. Johnson; Stanford M. Back

[57] ABSTRACT

Ruthenium carbonyl-cobalt carbonyl catalyst mixtures effectively catalyze the dealkoxyhydroxymethylation of aldehyde acetals, wherein said acetal may be prepared separately or in situ from an aldehyde and an alcohol. Methylal, for example, may be reacted with syngas, i.e., CO and $H_2$, in the presence of this ruthenium carbonyl-cobalt carbonyl catalyst to form the monomethyl ether of ethylene glycol.

The invention also is directed to the ruthenium carbonyl-promoted cobalt carbonyl catalysts per se, including novel precipitated forms of these ruthenium-cobalt carbonyl catalyst mixtures.

6 Claims, No Drawings

RUTHENIUM-COBALT CARBONYL CATALYSTS FOR THE DEALKOXYHYDROXYMETHYLATION OF ALDEHYDE ACETALS TO FORM GLYCOL ETHERS

CROSS-REFERENCE TO RELATED APPLICATION

This application is a continuation-in-part of Ser. No. 622,815, filed June 21, 1984.

BACKGROUND OF THE INVENTION

1. Scope of the Invention

This invention relates to the dealkoxyhydroxymethylation of aldehyde acetals. More particularly, it relates to a novel process for the dealkoxyhydroxymethylation of certain dialkyl-, dicycloalkyl-, diaryl-, or cyclic-aldehyde acetals by reacting said acetals with syngas, i.e., hydrogen and carbon monoxide, in the presence of novel ruthenium carbonyl-cobalt carbonyl catalysts to form the corresponding glycol monoethers. Still more particularly, it relates to the catalysts per se and methods for preparing the same. The acetals described herein may be prepared separately or formed in situ from the corresponding aldehyde and alcohol precursors.

The glycol ethers described herein encompass known classes of compounds having various uses, as for example as jet fuel additives, cleaners, coatings solvents, intermediates in the production of certain diphthalates, and the like.

2. Description of the Prior Art

One current well-known method of manufacturing ethylene glycol monoethers such as monoalkyl ethers consists of reacting ethylene oxide with the alcohol corresponding to the desired alkyl ether, employing various known catalyst systems.

Alternatively, the cobalt-catalyzed reaction of aldehydes or their dialkyl acetals with syngas, i.e., a carbon monoxide-hydrogen mixture, to form the corresponding glycol ether is also described in the art. Thus, for example, a method of making ethylene glycol ethers is described in U.S. Pat. No. 2,525,793 which employs cobalt oxide to catalyze the reaction of methylal with syngas to provide a reaction mixture which, after hydrogenation over nickel, gives relatively uneconomical conversions on the order of 25–33%.

Numerous attempts have been made to obtain more practical yields of glycol ethers from aldehydes or their dialkylacetals. A number of promoters have been used in conjunction with various cobalt catalysts in an effort to improve reaction rates and product yields. U.S. Pat. No. 4,062,898, for example, discloses a ruthenium chloride-promoted cobalt iodide catalyst which hydrocarbonylates formaldehyde dimethylacetal (methylal) to ethylene glycol monomethyl ether, (EGMME) in yields of 10% or less. The reaction temperature required is 185° at 20 atm. or above. A second method, described in Jpn. Kokai Tokkyo Koho 81 83,432, (1981) uses substantial quantities of 2,4,6-collidine or similar aromatic amines to promote the cobalt carbonyl-catalyzed hydrocarbonylation of methylal in benzene as a solvent. The reaction of methylal with highly pressurized syngas in this process at 190° C. for 10 hours gave 44% selectively to EGMME at 98% conversion. A further patent, Euro. Pat. Appln. EP 34,374. (1981) uses both iodine and triphenyl or tricyclohexylphosphine together with $RuCl_3.H_2O$ to promote the $Co(OAc)_2.4H_2O$—catalyzed hydrocarbonylation of methylal using 3000 psig of syngas, and temperatures of between 150° and 175° C. to obtain results nearly comparable to those of the Japanese.

More recently, Knifton has found that cobalt carbonyl promoted with a Group VIB donor ligand catalyzes the hydrocarbonylation of an aldehyde in an alcohol to make ethylene glycol monoethers; U.S. Pat. No. 4,308,403. Yields of ethylene glycol monobutyl ether (EGMBE) as high as 61 wt.% were reported in this patent. A cyclopentadienyl-ligated cobalt catalyst is also effective for these reactions giving glycol ethers in up to 54% yield; U.S. Pat. No. 4,317,943.

Propylene glycol monoalkylethers are formed by contacting high pressure mixtures of carbon monoxide and hydrogen with either an acetal or an aldehyde and an alcohol using a cobalt catalyst promoted with a tin- or germanium-containing compound; U.S. Pat. No. 4,356,327. Yields of glycol ethers up to 31 wt.% were reported in this patent. Ethylene glycol ethers were also formed from a formaldehyde acetal or formaldehyde and an alcohol using tin or germanium promoters for cobalt carbonyl; U.S. Pat. No. 4,357,477. The highest glycol ether yield (EGMBE) was 53% in this case.

Finally, propylene glycol monoalkyl ethers were formed by hydrocarbonylation of acetaldehyde acetals or acetaldehyde and alcohols using rhodium, ruthenium or nickel compounds to promote either cobalt carbonyls or cobalt compounds having group V ligand systems attached. Glycol ether yields up to 28 wt.% were realized when these promoters were used; Knifton, U.S. Pat. No. 4,390,734 (1983).

Thus, the use of various promoters for the cobalt-catalyzed hydrocarbonylation of aldehydes or acetals has resulted in glycol ether yields of from 10–61 wt.%, depending on the glycol ether produced. The highest reported yields of EGMME is 44%, of EGMBE is 61% and PGMEE is 28%.

SUMMARY OF THE INVENTION

In accordance with the present invention, there is provided an improved process for the reaction of certain dialkyl-, dicycloalkyl-, diaryl-, or cyclic-aldehyde acetals or their aldehyde-alcohol precursors with syngas in the presence of novel ruthenium carbonyl-cobalt carbonyl catalysts, to form the corresponding glycol monoethers. This reaction, which may best be described as the dealkoxyhydroxymethylation of an acetal, formed separately or in situ by the known reaction of an aldehyde with an alcohol, may be depicted by the following general reaction scheme:

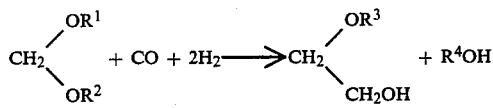

wherein $R^1$ and $R^2$, which may be the same or different, are alkyl, cycloalkyl, or aryl, or taken together form a cyclic acetal; $R^3$ is alkyl, cycloalkyl, aryl, or an hydroxy-substituted hydrocarbon moiety; and $R^4$ is alkyl, cycloalkyl, or aryl corresponding to whichever $R^1$ or $R^2$ group is displaced. In the case where cyclic acetals are employed, however, no alcohol by-product is formed.

Examples of $R^1$, $R^2$, $R^3$ or $R^4$ alkyl, cycloalkyl, and aryl groups which may be employed include such substituted or unsubtituted groups as:

(a) straight or branched chain alkyl groups, preferably those having from 1 to about 20 carbon atoms, such as methyl, ethyl, propyl, isopropyl, n-butyl, t-butyl, 2-ethylhexyl, dodecyl, and the like;

(b) substituted or unsubstituted cycloalkyl groups, preferably those having from about 5 to about 20 carbon atoms, such as cyclopentyl, cyclohexyl, cycloheptyl, 3-methylcyclopentyl, 3-butylcyclohexyl, cyclooctyl, adamantyl, decalyl, 3-phenylcycloheptyl and the like; and (c) substituted or unsubstituted aryl groups, preferably those having from 6 to about 20 carbon atoms such as benzyl, phenyl, naphthyl, fluoranthyl, tetralyl, tolyl, ethylphenyl, cumyl, anisyl, chlorophenyl, and the like.

It will be understood that when $R^1$ and $R^2$ in the foregoing reaction scheme are different, the resulting product will actually be mixtures of the corresponding glycol ethers and alcohols. It will also be understood, as mentioned above, that $R^1$ and $R^2$ may be joined by one or more bridging atoms to form a cyclic acetal, in which case, under the conditions of this reaction the heterocyclic ring will cleave at a carbon-oxygen bond of the acetal moiety, and hydroxymethylate, thereby forming a dihydroxy ether i.e., an hydroxy-substituted glycol ether.

This invention is also directed to novel ruthenium-carbonyl cobalt carbonyl catalysts per se, and to methods of preparing the same.

This process, using the novel catalysts of this invention, provides an improvement over the methods of the prior art in that the instant catalysts do not require the added presence of the iodide, amines, or phosphine promoters such as are disclosed in the prior art, and thus are less costly and easier to prepare and recover. Moreover, these novel catalysts permit the reaction to be carried out under mild conditions of time and temperature, yet most surprisingly provide rates and selectivities of desired product over those obtained by the use of cobalt carbonyl alone.

DESCRIPTION OF THE PREFERRED EMBODIMENTS

The novel catalysts of this invention are ruthenium carbonyldicobalt octacarbonyl mixtures, more specifically, triruthenium dodecacarbonyldicobalt octacarbonyl mixtures. This catalyst system is readily prepared by mixing dicobalt octacarbonyl, ($Co_2(CO)_8$), with ruthenium dodecacarbonyl, ($Ru_3(CO)_{12}$), in the reaction medium. The molar ratios of these two components are optimally in the range of about 10:1 to 1:10, and preferably about 5:1 to 1:5, and most preferably 1:1.

It has also been found, in accordance with this invention, that when the catalyst mixture is allowed to precipitate from the reaction medium following completion of the hydroxymethylation reaction this material unexpectedly has been found to have superior catalytic activity over the initial ruthenium-carbonyl-cobalt carbonyl mixture in terms of rates and selectivities. This activity has been found to vary somewhat, however, depending upon the rate at which the precipitate forms, along with other factors such as the initial concentrations, ratios, and the like. Thus, for example, when the ruthenium carbonyl and cobalt carbonyl are mixed into the reaction medium in molar ratios of 1:1, and the mixture allowed to precipitate out of solution, following dealkoxyhydroxymethylation, for a period of 1-25 days, the resulting solid, when used in a acetal-syngas reaction, provides equal or increased activity with respect to rates and selectivities for glycol monoethers.

Equally surprising, it has also been found that an even more active catalyst than the precipitate described above may be obtained by heating the ruthenium and cobalt mixture for periods of from about 1 to 5 hours in the presence of an inert organic solvent, preferably a chlorinated aromatic such as chlorobenzene, o-dichlorobenzene, or the like, under pressurized syngas. The mixture, on cooling, results in an orange-colored precipitate, which when used as a catalyst in the dealkoxyhydroxymethylation of methylal, results in significant improvements in the rates and selectivities for the ethylene glycol ether over the original catalyst mixture. For example, when ruthenium carbonyl and cobalt carbonyl are mixed in molar ratios of 1:1, heated in chlorobenzene at about 150° C. under 3000 psi of syngas for about 3 hours, and then cooled, the resulting precipitate has increased catalytic activity in a dealkoxyhydroxymethylation reaction.

The aldehyde acetal dealkoxyhydroxymethylation reaction with syngas, as described above, utilizing the novel ruthenium-carbonyl-cobalt carbonyl catalyst mixtures of this invention including the aforedescribed precipitated forms thereof, may conveniently be conducted in a generally known manner whereby the desired acetal is reacted with syngas under elevated temperature and pressures for given periods of time, during which period the reaction mixture is actively stirred. In this reaction, the volume ratio of carbon monoxide to hydrogen in the syngas desirably is in the range of from about 1:5 to 5:1, and more preferably 1:3 to 3:1. Following rapid cooling, the reaction product is then recovered from the mixture in a routine manner.

In contrast to the prior art reaction conditions described above, the novel ruthenium-carbonyl-cobalt carbonyl catalysts of this invention advantageously permit the use of more mild operating conditions. Thus, temperatures in the range of from about 100° to 200° C., and preferably about 125° to 175° C., pressures of from about 500 to 5000 psi, and preferably about 1000 to 3000 psi, may satisfactorily be employed. The reaction time is not critical, and may range up to several hours, desirably about 1-4 hours.

The weight ratio, in grams, of catalyst mixture to acetal, is desirably in the range of from about 1:1000-10:1, and preferably in the range of from about 1:100-1:1 in a batch reaction.

In a further embodiment of this invention, it has been found that highly advantageous effects may also be obtained in this dealkoxyhydroxymethylation process by the use of solvents with the acetal. The solvents which may be advantageously used comprise any polar or non-polar organic solvents which are inert to the conditions of the reaction. Included amongst these solvents are $C_{1-12}$ alcohols, preferably those corresponding to the alkyl group of the formaldehyde acetal, such as methanol, ethanol, butanol, 3-ethyl-2-hexanol and the like; ethers which will not cleave under the conditions of the reaction, such as glyme, diglyme, diphenyl ether and the like; aromatics and substituted aromatics such as benzene, toluene, xylene, chlorobenzene, dichlorobenzene, anisole, and the like.

The solvents maybe employed in the amounts of up to 90 volume percent of the reaction mixture, and preferably in amounts of about 20 to 80 percent.

The acetal starting materials employed in this invention have the aforedescribed general formula, namely

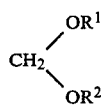

wherein $R^1$ and $R^2$ are as defined above. These acetals can be prepared in a known manner, separately or in situ, as for example as described in E. V. Dehmlav and J. Schmidt, Tetrahedron Letters, p. 95–6 (1976) B. S. Bal and H. W. Pinnick, J. Org. Chem. V44 (21), p. 3727–8 (1979) D. W. Hall, U.S. Pat. No. 3,492,356, Jan. 27 (1970), by the reaction of formaldehyde with an alcohol, or mixture of alcohols, of the general formula $R^1OH$ or $R^2OH$, where again $R^1$ and $R^2$ are as defined above, to form the corresponding acetal. In the case of cyclic acetals the alcohol must be a diol. Hereinafter, when the acetal is referred to, it will be understood that the corresponding precursors, aldehyde and the desired alcohol, are also intended to be included.

As mentioned above, the $R^1$ and $R^2$ groups of the acetal may comprise a bridging group to form such cyclic acetals as

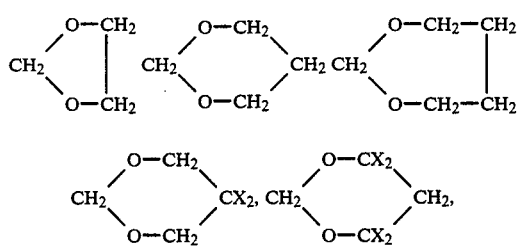

and the like, wherein X is selected from the group consisting of alkyl, aralkyl, aryl and cycloalkyl groups, preferably those having from 1 to about 20 carbon atoms. As described above, cleavage of the ring under the conditions of this reaction will result in the formation of the corresponding hydroxy-substituted glycol ether.

Illustrations of products thus formed from cyclic acetals include, for example, diethylene glycol from dioxolane, the conversion of 2- or 4-methyldioxolane to the corresponding hydroxy glycol ether, and the like.

It is important, in selecting the acetal starting material, that it not contain any substituents which would adversely affect the reaction. In other words, the $R^1$ and $R^2$ groups should not, for example, contain such reactive moieties as phosphine, arsine, amino, sulfido or carbonyl groups, acetal moieties, or olefins or acetylenic double bonds. Other like groups will be recognized or readily determined by those skilled in the art as resulting in products other than the desired monoethers. On the other hand, halogen, alkoxy, and hydroxy moieties and the like may be present on the hydrocarbon substituents without adverse effect.

When these acetals are dealkoxyhydroxymethylated with syngas in accordance with the process of this invention, there are obtained the corresponding glycol monoethers in which the ether moiety will correspond to the R groups of the acetal starting material. Also formed in lesser amounts are a tri-substituted ethane of the general formula

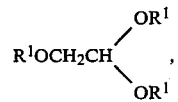

wherein $R^1$ (or, alternatively, $R^2$, or mixtures of $R^1$ and $R^2$) is as defined above, which may be recycled to form additional acetal starting material, and alcohol by-products. Again, as above, if the $R^1$ and $R^2$ groups of the acetal are different, a mixture of corresponding R-substituted compounds will result. This tri-substituted ethane is believed to form during the reaction from an alkoxyacetaldehyde, e.g., the intermediate methoxyacetaldehyde, when methylal is used, ethoxyacetaldehyde when ethylal is used, and the like.

As shown below, the selectivities for the desired monoether over the tri-substituted by-product are in the ratio of from about 3:1 to as much as 10:1 or more.

In a preferred embodiment of this invention, the starting materials are preferably symmetrical acetals where the $R^1$ and $R^2$ groups are lower alkyl groups of 1 to about 4 carbon atoms, thereby forming the corresponding glycol mono-lower alkyl ethers such as the monomethyl ether, the monoethyl ether, and the like.

Alternatively, the acetal may contain such $R^1$ and $R^2$ groups as naphthyl and phenyl. In the case of naphthyl, the reaction of the formaldehyde acetal with syngas will provide 2-(2-naphthyloxy)ethanol, a known sedative, which in turn may be oxidized to the corresponding 2-naphthyloxyacetic acid, a plant growth hormone.

Likewise, the dealkoxyhydroxymethylation of the acetal, wherein $R^1$ and $R^2$ are phenyl, will produce 2-phenoxy-ethanol, a topical antiseptic, which when oxidized, results in phenoxyacetic acid, a fungicide. Similarly, the formaldehyde acetal wherein $R^1$ and $R^2$ are of 2,4,5-trichlorophenyl will yield, 2,4,5-trichlorophenoxyacetic acid, an herbicide. In a like manner, when $R^1$ and $R^2$ are p-nonylphenyl, p-nonylphenoxyacetic acid, a corrosion inhibitor and antifoaming agent in gasoline and cutting oils will be formed.

Each of these aforedescribed products may be recovered routinely by methods well known in the art.

The invention will now be illustrated by, but is not intended to be limited to, the following examples.

EXAMPLES

EXAMPLES 1-21

A series of runs was carried out in which the general procedure described below was employed, using as the catalyst a mixture of $Co_2(CO)_8$ and $Ru_3(CO)_{12}$, or $Co_2(CO)_8$ alone (for comparative purposes). In Table I, it should be noted that whereas addition of $Ru_3(CO)_{12}$ caused an increase in production of the glycol ether, B, over that obtained with $Co_2(CO)_8$ alone, other metal carbonyls had no such effect. Formed in lesser amounts was trimethoxyethane, A; however, the selectivity of B over A was significantly better in almost all cases where the catalysts of this invention were employed.

To a 300 ml stainless steel autoclave equipped with a magnedrive stirrer was charged: 55 cc of a solution of methylal, solvent (as indicated) and catalyst. Carbon monoxide 800 psig, and hydrogen, 1600 psig, were admitted and the reaction mixture was rapidly heated to the desired temperature. The mixture was stirred for the designated time at reaction temperature after which the reactor was cooled by immersion in an ice bath. When the contents reached 25° C. the final pressure was recorded. After venting the gas the liquid was analyzed by GLPC.

The results are reported in Table I below. Reaction conditions, amounts, and the use of solvents were varied in accordance with the data set forth in this table.

to 150° C. The reaction mixture was stirred for the designated time period and then rapidly cooled, the pressure released, gases collected and analyzed by GC/MS and the liquid removed and analyzed by standardized glpc.

The results of these runs are reported in Table II below.

TABLE I
ETHYLENE GLYCOL MONOMETHYL ETHER VIA DEALKOXYHYDROXYMETHYLATION OF METHYLAL

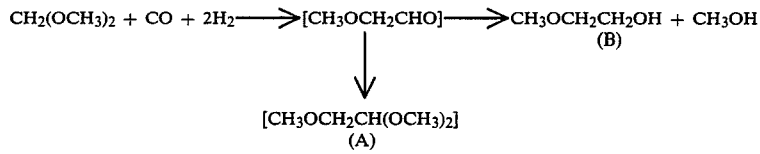

$$CH_2(OCH_3)_2 + CO + 2H_2 \longrightarrow [CH_3OCH_2CHO] \longrightarrow CH_3OCH_2CH_2OH + CH_3OH$$
(B)

$$[CH_3OCH_2CH(OCH_3)_2]$$
(A)

| Examples | $Co_2(CO)_8$ (gms.) | $Ru_3(CO)_{12}$ (gms.) | OTHER CATS. (2 gms.) | SOLVENT | METHYLAL Vol. % | T, °C. | T, HRS. | P (psig) | CONV. % | SELECTIVITY, % (A) | (B) |
|---|---|---|---|---|---|---|---|---|---|---|---|
| 1 | 2 | 0 | — | None | 100 | 110 | 4 | 1480 | 68 | 33 | 3 |
| 2 | 2 | 2 | — | None | 100 | 110 | 2.5 | 1358 | 77 | 19 | 16 |
| 3 | 2 | 0 | — | None | 100 | 150 | 1 | 1535 | 92 | 7 | 22 |
| 4 | 2 | 2 | — | None | 100 | 150 | 1 | 1617 | 88 | 7 | 37 |
| 5 | 2 | 0 | — | None | 100 | 150 | 2.5 | 1885 | 95 | 2 | 20 |
| 6 | 2 | 2 | — | None | 100 | 150 | 2.5 | 1721 | 95 | 7 | 37 |
| 7 | 1 | 2 | — | None | 100 | 150 | 4 | 1816 | 93 | 2 | 38 |
| 8 | 1 | 0 | — | None | 100 | 150 | 2.5 | 1847 | 89 | 2 | 18 |
| 9 | 1 | 2 | — | None | 100 | 150 | 2.5 | 1840 | 87 | 3 | 34 |
| 10 | 1 | 0 | $Os_3(CO)_{12}$ | None | 100 | 150 | 1 | 1410 | 81 | 7 | 19 |
| 11 | 1 | 0 | $Fe(CO)_5$ | None | 100 | 150 | 1 | 1310 | 81 | 7 | 16 |
| 12 | 1 | 0 | $Ir_4(CO)_{12}$ | None | 100 | 150 | 1 | 1469 | 79 | 7 | 15 |
| 13 | 1 | 0 | $Re_2(CO)_{10}$ | None | 100 | 150 | 1 | 1274 | 70 | 16 | 13 |
| 14 | 1 | 0 | $Cr(CO)_6$ | None | 100 | 150 | 1 | 1439 | 73 | 10 | 13 |
| 15 | 1 | 0 | $Fe_3(CO)_{12}$ | None | 100 | 150 | 1 | 1310 | 79 | 6 | 13 |
| 16 | 1 | 0 | $RhCl_3$ | None | 100 | 150 | 4 | 916 | 57 | 12 | 4 |
| 17 | 1 | 0 | — | THF[1] | 45 | 150 | 2 | 1252 | 96 | 2 | 19 |
| 18 | 1 | 2 | — | THF | 45 | 150 | 4 | 1257 | <99 | 1 | 40 |
| 19 | 1 | 0 | — | Toluene | 45 | 150 | 3 | 707 | 76 | 7 | 24 |
| 20 | 1 | 0 | — | DMF[2] | 45 | 150 | 4 | 116 | 74 | TR | 0.3 |
| 21 | 0 | 2 | — | None | 100 | 150 | 2.5 | 106 | 1 | 1 | 0.2 |

[1]THF = Tetrahydrofuran
[2]DMF = Dimethylformamide

TABLE II
CATALYTIC DEALKOXYHYDROXYMETHYLATION OF METHYLAL USING COBALT-RUTHENIUM CARBONYLS

| EXAMPLE | $Co_2(CO)_8$ (gms.) | $Ru_3(CO)_{12}$ (gms.) | OTHER, gms. | METHYLAL (gms.) | $P_{total}$[f] (psig) | $CO/H_2$ Ratio | T °C. | T HRS. | SELECTIVITY TO $C_2$, %[a] | $C_2$ Ratio[b] | METHYLAL CONV., % |
|---|---|---|---|---|---|---|---|---|---|---|---|
| 22 | 1.5 | 3.0 | — | 71.4 | 2445 | ½ | 150 | 2.0 | 45.4 | 9.0 | 70.1 |
| 23 | — | — | [c], 2.5 | 59.3 | 2430 | ½ | 150 | 3.0 | 55.3 | 11.8 | 73.7 |
| 24 | — | — | [d], 2.0 | 47.3 | 2415 | ½ | 150 | 4.0 | 67.2 | 3.7 | 64.6 |
| 25 | — | — | [e], 18.4 | 71.4 | 2432 | ½ | 150 | 3.0 | 65.2 | 7.4 | 60.4 |

[a]Selectivity = (moles of $CH_3OCH_2CH_2OH$ + $CH_3OCH_2CH(OCH_3)_2$ formed/moles of $CH_2(OCH_3)_2$ reacted).
[b]$C_2$ ratio = moles of $CH_3OCH_2CH_2OH$/moles of $CH_3OCH_2CH(OCH_3)_2$.
[c]Catalyst isolated by precipitation from solutions of Co—Ru catalyzed methylal dealkoxyhydroxymethylations in which THF was used as the solvent. (See Examples 23 catalyst preparation below.)
[d]Catalyst isolated by precipitation from solutions of Co—Ru catalyzed methylal dealkoxyhydroxymethylations carried out in neat methylal. (See Example 24 catalyst preparation below.)
[e]Catalyst prepared by heating a mixture of $[Co_2(CO)_8]$, 2 gms. and $[Ru_3(CO)_{12}]$, 4 gms. in chlorobenzene at 150° C. under 3000 psi of syngas ($CO/H_2 = \frac{1}{2}$) for 3 hrs. On cooling 2gms. of brick-orange solid precipitated (See Example 25 catalyst preparation below.)
[f]$P_{Total}$ = Total pressure uptake during reaction at 150° C. (psig).

EXAMPLES 22-25

In addition to the above runs, another series of runs was carried out in accordance with the following general procedure, using varying conditions, in which the catalyst employed was precipitated from solutions of cobalt carbonyl-ruthenium carbonyl catalyzed methylal dealkoxyhydroxymethylation, as shown in the catalyst preparations which follow Table II.

The catalyst system and methylal were charged to a 300 ml autoclave and the system flushed thoroughly with CO and $H_2$. A 1:1 $CO/H_2$ mixture was added to a pressure of 2400 psig and the temperature rapidly raised The catalysts for Examples 23, 24 and 25 of Table II were prepared as follows:

EXAMPLE 23 CATALYST

The catalyst for Example 23 was prepared by allowing the liquid recovered from two runs identical to Example 18, Table 1, to stand for several weeks, after which an orange solid precipitated. Filtration of the orange solid followed by drying in vacuo gave a material which exhibited characteristic metal carbonyl bands in the infrared but was neither $Co_2(CO)_8$ nor $Ru_3(CO)_{12}$. The IR bands in the isolated solid were at 4.83, 4.92 and 4.98μ. The bridging carbonyl of the starting $Co_2(CO)_8$ (5.37μ) had totally disappeared in forming the new active complex. The solid, 2.5 grams, was used as a catalyst for Example 23.

EXAMPLE 24 CATALYST

The catalyst for Example 24 was prepared by allowing the liquid recovered from two runs identical to Example 4, Table 1, to stand for several weeks after which an orange solid precipitated. This solid, 2.0 grams, after filtration and drying in vacuo, was used as the catalyst for Example 24. The solid which was isolated had characteristic metal carbonyl IR bands at 4.83, 4.92 and 4.98μ. The bridging carbonyl of the starting $Co_2(CO)_8$ had completely disappeared.

EXAMPLE 25 CATALYST

The catalyst for Example 25 was prepared as indicated in footnote (c) of Table II. The isolated orange solid had IR bands at 4.83μ, 4.92μ an 4.97μ indicative of a metal carbonyl complex in which there was no bridging carbonyl band at 5.37μ.

In the following examples, Examples 26–32, experiments were carried out in a manner similar to Examples 1–25, except that dibutoxymethane was substituted for methylal, and solvents and temperatures were varied as shown in Tables III and IV, to produce ethylene glycol monobutyl ether.

EXAMPLES 26–29

In Examples 26–29 formaldehyde dibutylacetal, $(CH_2(OBu)_2)$, was dealkoxylhydroxymethylated to ethylene glycol monobutyl ether, EGMBE, using a 1:1 mixture of $Co_2(CO)_8$ and $Ru_3(CO)_{12}$ as the catalyst. It can be seen from the tabulated results of Table III that running the reaction in a solvent such as n-butyl alcohol or o-dichlorobenzene gives generally superior yields to running the reaction in neat $CH_2(OBu)_2$.

In Table III, the examples were conducted in accordance with the following general procedure:

Dicobalt octacarbonyl, 4 mmoles, triruthenium dodecacarbonyl, 4 mmoles, plus $CH_2(OBu)_2$ and solvent in the amounts listed in the table were charged to a 300 ml stirred autoclave to which 3200 psi of a 1:1 mixture of CO and $H_2$ were added and then heated to 150° C. for 3–4 hrs. The autoclave was cooled, drained and the product weighed and subjected to standardized gas chromatographic analysis (G.C.).

TABLE III

EFFECTS OF SOLVENTS ON DEALKOXYHYDROXYMETHYLATION OF BUTYLAL
G. C. Analysis Reaction Mixture, Area %

| Exam. | Solvents | $CH_2(OBu)_2$ Used, (ml) | (ml) | $CH_3OBu$ | $PhCH_3^{(a)}$ | BuOH | $CH_2(OBu)_2$ | EGMBE[b] |
|---|---|---|---|---|---|---|---|---|
| 26 | None | 0 | 90 | 6.0 | 19.1 | 33.3 | 6.7 | 18.8 |
| 27 | n-BuOH | 45 | 45 | 2.5 | 17.2 | 61.6 | trace | 13.7 |
| 28 | n-BuOH | 67 | 23 | 0.9 | 16.4 | 73.8 | trace | 4.8 |
| 29 | o-$Cl_2C_6H_4^{(f)}$ | 67 | 23 | 0.9 | 18.0 | 5.7 | trace | 5.0 |

| Exam. | TBE[c] | Unidentified Heavies | Solvent | Conv. of $CH_2(OBu)_2$ Mole % | Selectivity to EGMBE Mole % | Yield[d] of EGMBE Mole % |
|---|---|---|---|---|---|---|
| 26 | 4.3 | 7.3 | | 94 | 32 | 30 |
| 27 | 3.2 | 1.8 | | <99 | 44 | 44 |
| 28 | 1.0 | 3.2 | | <99 | 28 | 28[e] |
| 29 | 0.3 | 0.9 | 69.1 | <99 | 42 | 42 |

[a]$PhCH_3$ is the internal standard
[b]EGMBE — ethylene glycol monobutyl ether
[c]TBE — 1,1,2-tributoxyethane
[d][(mmoles EGMBE in recovered liquid)/(mmoles $CH_2(OBu)_2$ charged)] × 100
[e]low product yield due to mechanical losses
[f]o-$Cl_2C_6H_4$—o-dichlorobenzene

EXAMPLES 30–32

In Examples 30–32, the results of which are summarized in Table IV, it can be seen that as the reaction temmperature is raised from 125° to 175° C. the EGMBE yield increases from 12 to 34 mol%.

In Table IV, the examples were conducted in accordance with the following general procedure:

Dicobalt octacarbonyl, 4 mmoles, triruthenium dodecacarbonyl, 4 mmoles, and $CH_2(OBu)_2$, 90 ml, were charged to a 300 ml autoclave. Then 3200 psi of a 1:1 CO/$H_2$ mixture was added and the reaction mixture heated for 3–4 hours at the temperature listed in the Table. The autoclave was cooled, drained and the product weighed and subjected to standardized gas chromatographic analysis.

TABLE IV

EFFECTS OF TEMPERATURE ON DEALKOXYHYDROXYMETHYLATION OF BUTYLAL
G. C. Analysis Reaction Mixture, Area %

| Ex. | [$Co_2(CO)_8$] (mmoles) | [$Ru_3(CO)_{12}$] (mmoles) | T, °C. | $CH_2(OBu)$ Used, (ml) | $CH_3OBu$ | $PhCH_3^{(a)}$ | BuOH | $CH_2(OBu)_2$ |
|---|---|---|---|---|---|---|---|---|
| 30 | 4 | 4 | 125 | 90 | 1.8 | 17.0 | 20.1 | 30.5 |
| 31 | 4 | 4 | 150 | 90 | 6.0 | 19.1 | 33.3 | 6.7 |
| 32 | 4 | 4 | 175 | 90 | 11.1 | 18.3 | 35.0 | 3.3 |

TABLE IV-continued

EFFECTS OF TEMPERATURE ON DEALKOXYHYDROXYMETHYLATION OF BUTYLAL

G. C. Analysis Reaction Mixture, Area %

| Ex. | EGMBE[b] | TBE[c] | Unidentified Heavies | Conv. of $CH_2(OBu)_2$ Mole % | Selectivity to EGMBE Mole % | Yield[d] of EGMBE Mole % |
|---|---|---|---|---|---|---|
| 30 | 7.1 | 10.4 | 10.6 | 69 | 17 | 12 |
| 31 | 18.8 | 4.3 | 7.3 | 94 | 32 | 30 |
| 32 | 20.8 | 2.6 | 3.3 | 97 | 35 | 34 |

[a]$PhCH_3$ is the internal standard
[b]EGMBE — ethylene glycol monobutyl ether
[c]TBE — 1,1,2-tributoxyethane
[d][(mmoles EGMBE in recovered liquid)/(mmoles of $CH_2(OBu)_2$ charged)] × 100

EXAMPLE 33

Using the procedures of Example 31, except that formaldehyde dicyclohexyl acetal is used instead of formaldehyde dibutyl acetal, ethylene glycol monocyclohexyl ether is prepared in good yield.

EXAMPLE 34

Using the procedures of Example 31, except that formaldehyde diphenyl acetal is used instead of formaldehyde dibutyl acetal, ethylene glycol monophenyl ether is formed as a reaction product.

EXAMPLE 35

Using the procedures of Example 31, except that the cyclic acetal dioxolane is used instead of formaldehyde dibutyl acetal, diethyleneglycol is produced as a reaction product.

EXAMPLE 36-43

Approximately 6 grams of paraformaldehyde and the catalysts indicated in Table V in 90 ml of butanol and 10 ml of toluene were heated at the temperatures given in Table V at the pressures of hydrogen and CO indicated for two hours. After this time the reaction mixtures were analyzed by gas chromatography showing the major product to be ethylene glycol monobutyl ether. The results are tabulated in Table V.

TABLE V

REACTIONS OF PARAFORMALDEHYDE, SYNGAS AND BUTANOL TO GIVE ETHYLENEGLYCOL MONOBUTYL ETHER, EGMBE[a]

| EXAMPLE | CATALYST COMPONENTS | | INITIAL PRESSURES | | REACTION T. °C. | REACTION PRODUCTS (GC Area %) | | |
|---|---|---|---|---|---|---|---|---|
|  | $Co_2(CO)_8$ (mmoles) | $Ru_3(CO)_{12}$ (mmoles) | $H_2$ | CO |  | $CH_3OC_5H_9$ | EGMBE | $CH_2(OC_4H_9)_2$ |
| 36 | 4 | 4 | 1600 | 800 | 150 | 2.0 | 9.4 | tr |
| 37 | 4 | 4 | 1600 | 800 | 150 | 2.0 | 9.7 | 0.3 |
| 38 | 2 | 4 | 1600 | 800 | 150 | 1.7 | 9.6 | 0.5 |
| 39 | 2 | 4 | 1600 | 800 | 150 | 1.4 | 9.1 | 1.5 |
| 40 | 4 | 4 | 1600 | 1600 | 150 | 1.2 | 10.7 | 0.5 |
| 41 | 4 | 4 | 1600 | 1600 | 150 | 0.7 | 9.2 | 1.8 |
| 42 | 2 | 4 | 1600 | 1600 | 150 | 0.7 | 9.2 | 1.8 |
| 43 | 4 | 4 | 1600 | 800 | 175 | 2.3 | 9.6 | — |

[a]EGMBE = Ethylene glycol monobutyl ether

EXAMPLES 44–45

Increased yields of glycol ethers can be obtained by increasing dilution of the catalysts in o-dichlorobenzene, as shown by the following experiment.

Butylal, $CH_2(OC_4H_9)_2$, was dealkoxyhydroxymethylated by pressuring 3200 psig of 1/1 syngas into a solution of 79 mmoles of butylal in 79 ml of o-dichlorobenzene and the catalysts designated below, heating the mixture to 150° C. and stirring at that temperature for 6 hours, cooling and analyzing the reaction mixture. Results are given below.

TABLE VI

| Example | Catalyst $Co_2(CO)_8$ | $Ru_3(CO)_{12}$ | $C_4H_9OCH_2CHOH$ Wt. % Yield |
|---|---|---|---|
| 44 | 2 | 0 | 38.0 |
| 45 | 2 | 6 | 62.3 |

It will be seen that whereas the cobalt catalyst alone provides a yield of 38%, the combination of cobalt and ruthenium gives over 62%.

What I claim is:

1. A catalyst composition prepared by precipitating a ruthenium and cobalt carbonyl complex from a reaction mixture formed by the dealkoxyhydroxymethylation of an aldehyde acetal with syngas in the presence of a catalyst comprising a mixture of $Co_2(CO)_8$ and $Ru_3(CO)_{12}$, after recovering the reaction product and allowing the remaining liquid medium to stand for a time sufficient to precipitate said catalyst complex having IR bands at 4.83μ, 4.92μ, and 4.98μ.

2. The composition of claim 1 wherein the molar ratio of the cobalt to ruthenium carbonyl components of the precipitated catalyst is in the range of from about 10:1 to 1:10.

3. A catalyst composition prepared by precipitating a ruthenium and cobalt carbonyl complex from a reaction mixture formed by the dealkoxylhydroxymethylation of an aldehyde acetal with syngas in the presence of an inert organic solvent and a catalyst comprising a mixture of $Co_2(CO)_8$ and $Ru_3(CO)_{12}$, after recovering the reaction product and allowing the remaining liquid medium to stand for a time sufficient to precipitate said catalyst complex having IR bands at 4.83μ, 4.92μ, and 4.98μ or 4.83μ, 4.92μ, and 4.97μ.

4. The composition of claim 3 wherein the molar ratio of the cobalt to ruthenium carbonyl components of the precipitated catalyst is in the range of from about 10:1 to 1:10.

5. A catalyst composition prepared by precipitating a ruthenium and cobalt carbonyl complex from a reaction mixture formed by the treatment of a mixture of $Co_2(CO)_8$ and $Ru_3(CO)_{12}$ in a chlorinated aromatic hydrocarbon with syngas at elevated temperature and pressure and allowing the reaction mixture to stand for a time sufficient to precipitate said catalyst complex having IR bands at $4.83\mu$, $4.92\mu$, and $4.98\mu$.

6. The composition of claim 5 wherein the molar ratio of the cobalt to ruthenium carbonyl components of the precipitated catalyst is in the range of from about 10:1 to 1:10.

* * * * *